March 25, 1969 J. H. ASPER Plant Pat. 2,875
CAMELLIA PLANT
Filed Sept. 1, 1967
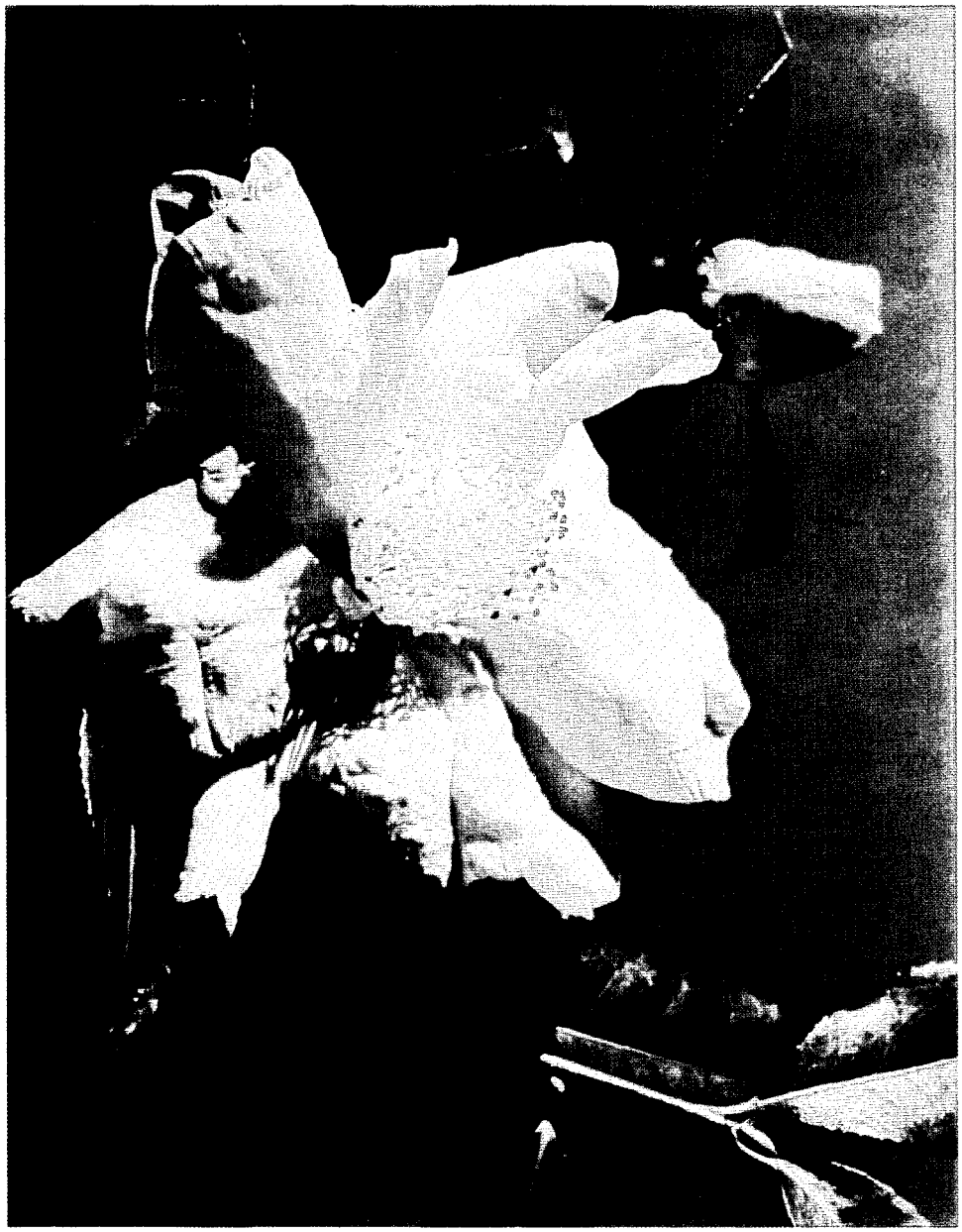
INVENTOR.
JAMES HOWARD ASPER
BY Rummler & Snow
ATTYS.

United States Patent Office

Plant Pat. 2,875
Patented Mar. 25, 1969

2,875
CAMELLIA PLANT

James Howard Asper, Escondido, Calif., assignor to Monrovia Nursery Company, Azusa, Calif., a corporation of California Filed Sept. 1, 1967, Ser. No. 665,190
Int. Cl. A01h 5/02
U.S. Cl. Plt.—61 1 Claim

ABSTRACT OF THE DISCLOSURE

A new camellia hybrid having a relatively large medium pink flower with a loose and open center arrangement of large petals, characterized by its early and profusely blooming habit and vigorous plant growth.

BACKGROUND OF THE INVENTION

My new variety of camellia plant originated as a seedling of *C. sasanqua* Narumigata (unpatented) × *C. reticulata* Lion Head (unpatented) and was discovered by me in 1960 in the course of a breeding program carried on by me at Escondido, Calif. since 1957 with the object of producing an improved variety of camellia plant which combines the plant vigor and early blooming habit of *C. sasanqua* with the large flower and exquisite beauty of *C. reticulata*. This new plant was observed to have the plant vigor desired and to produce a large and beautiful flower of unusual form, which prompted further testing to determine its fixed characteristics.

The new variety has been asexually propagated by me and under my direction at Escondido, Calif., by grafting and by means of cuttings, and successive generations have demonstrated that its novel characteristics are fixed and hold true generation to generation.

DESCRIPTION OF THE DRAWING

My new variety of camellia plant is illustrated in the accompanying photographic drawing in which a bud and a fully opened bloom are shown, in substantially natural color, together with some of the foliage.

DESCRIPTION OF THE INVENTION

The following is a detailed description of my new variety of camellia plant, the color designation for the bud and bloom being according to the Horticultural Colour Chart of the British Colour Council.

*The plant*

Origin: Seedling.
Parentage:
*Seed parent.*—*C. sasanqua* Narumigata.
*Pollen parent.*—*C. reticulata* Lion Head.
Classification: Hybrid.
Form: Bush, study and upright.
Height: Eight feet.
Growth: Vigorous, upright and branching.
Foliage:
*Quantity.*—Abundant.
*Size of leaf.*—3 inches long x 1¾ inches wide.
*Shape of leaf.*—Elliptic-lanceolate, with serrated margins.
*Texture.*—Leathery.

*Color.*—Upper side—dark green. Under side—light green.
*Petioles.*—¼ inch long.
*Ribs and veins.*—Prominent.

*Bud*

Form: Ovoid.
Size: 1½ inches long, 1 inch wide. Opens slowly.
Color: Scarlet 19/2—when sepals first divide and when petals begin to unfurl.
Sepals: Hooded over bud. Branched and upstanding. Color—pale green, inside and outside.
Calyx: Funnel shaped and broad, with hairy aspect. Does not split.
Peduncle: 1/16 inch long. Erect and hairy. Color—pale green.

*The flower*

Blooming habit: Continuous and profusely from early fall into winter in its natural habitat.
Size: Medium, 5½ inches in diameter and 2¾ inches deep.
Borne: Singly.
Shape: Flat, with high center, becoming more flat as bloom matures.
Petalage:
*Number of petals.*—12.
*Arrangement.*—Loose, with open center.
*Size.*—2½ inches long x 1½ inches wide.
*Color.*—Scarlet 19/2 on inside, reverse side and at base.
*Appearance.*—Satiny.
Petaloids: None.
Peduncle: 1/16" long. Sturdy and upright. Color—brownish-green.
Discoloration: Color fades slightly, after full bloom.
Fragrance: Slight.
Lasting quality: Seven days on plant; two days as a cut flower.
Persistence: Does not hang on and dry. Not affected by hot or wet weather and, as observed at Escondido, Calif., the blooms appear to be subject to no disease.

*Reproductive organs*

Stamens:
*Anthers.*—Number 156. Length—1/32 inch. Arrangement—bunched.
*Filaments.*—Length—1/32 inch. Color—pale yellow.
Pollen: Color—golden yellow.
Pistils: Three in number, each ⅝ inch long.
Stigmas: Color—light green.
Ovaries: Joined characteristic.

*Fruit*

The fruit is fertile, round in shape and of brown color at maturity.

I claim:

1. A new and distinct variety of camellia plant substantially as herein shown and described, characterized by its vigorous growth habit and its early blooming, relatively large, pink flowers with few but large petals loosely arranged about an open center.

No references cited.

ROBERT E. BAGWILL, *Primary Examiner.*